United States Patent
Gagel

(10) Patent No.: US 10,881,776 B2
(45) Date of Patent: Jan. 5, 2021

(54) CONTROL UNIT FOR DETECTING BLOOD IN A DIALYSATE DISCHARGE LINE OF A BLOOD TREATMENT DEVICE, AND BLOOD TREATMENT DEVICE

(71) Applicant: FRESENIUS MEDICAL CARE DEUTSCHLAND GMBH, Bad Homburg (DE)

(72) Inventor: Alfred Gagel, Litzendorf (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 16/314,643

(22) PCT Filed: Jun. 28, 2017

(86) PCT No.: PCT/EP2017/066039
§ 371 (c)(1),
(2) Date: Dec. 31, 2018

(87) PCT Pub. No.: WO2018/002162
PCT Pub. Date: Jan. 4, 2018

(65) Prior Publication Data
US 2019/0255241 A1 Aug. 22, 2019

(30) Foreign Application Priority Data
Jun. 29, 2016 (DE) .................. 10 2016 007 828

(51) Int. Cl.
*A61M 1/16* (2006.01)
*A61M 1/34* (2006.01)

(52) U.S. Cl.
CPC .......... *A61M 1/1692* (2013.01); *A61M 1/165* (2014.02); *A61M 1/1635* (2014.02); *A61M 1/3413* (2013.01); *A61M 1/3431* (2014.02); *A61M 2205/15* (2013.01); *A61M 2205/705* (2013.01)

(58) Field of Classification Search
None
See application file for complete search history.

(56) References Cited

U.S. PATENT DOCUMENTS 6,156,002 A * 12/2000 Polaschegg ............. A61M 1/16
210/646
2011/0089112 A1 4/2011 Sternby
2013/0313194 A1 11/2013 Lannoy

FOREIGN PATENT DOCUMENTS

| DE | 102013104501 | 11/2014 |
|----|----|----|
| EP | 0604753 | 7/1994 |
| EP | 0623357 | 11/1994 |

* cited by examiner

*Primary Examiner* — Richard C Gurtowski
(74) *Attorney, Agent, or Firm* — Jacobson Holman PLLC

(57) ABSTRACT

The invention relates to a control unit (30) for detecting an overshoot of a first limit value (G1) of a first blood concentration (B1) in a first portion (17a) of a dialysate discharge line (17) downstream of a dialysate chamber (7) of a dialyser (4) of a blood treatment device and upstream of a node point (110) at which a bypass line (100) bypassing the dialyser (4) leads into the dialysate discharge line (17), wherein the bypass line (100) branches off, upstream of the dialysate chamber (7), from a dialysate supply line (15) suitable for supplying dialysate from a dialysate source (16) to the dialysate chamber (7).

7 Claims, 1 Drawing Sheet

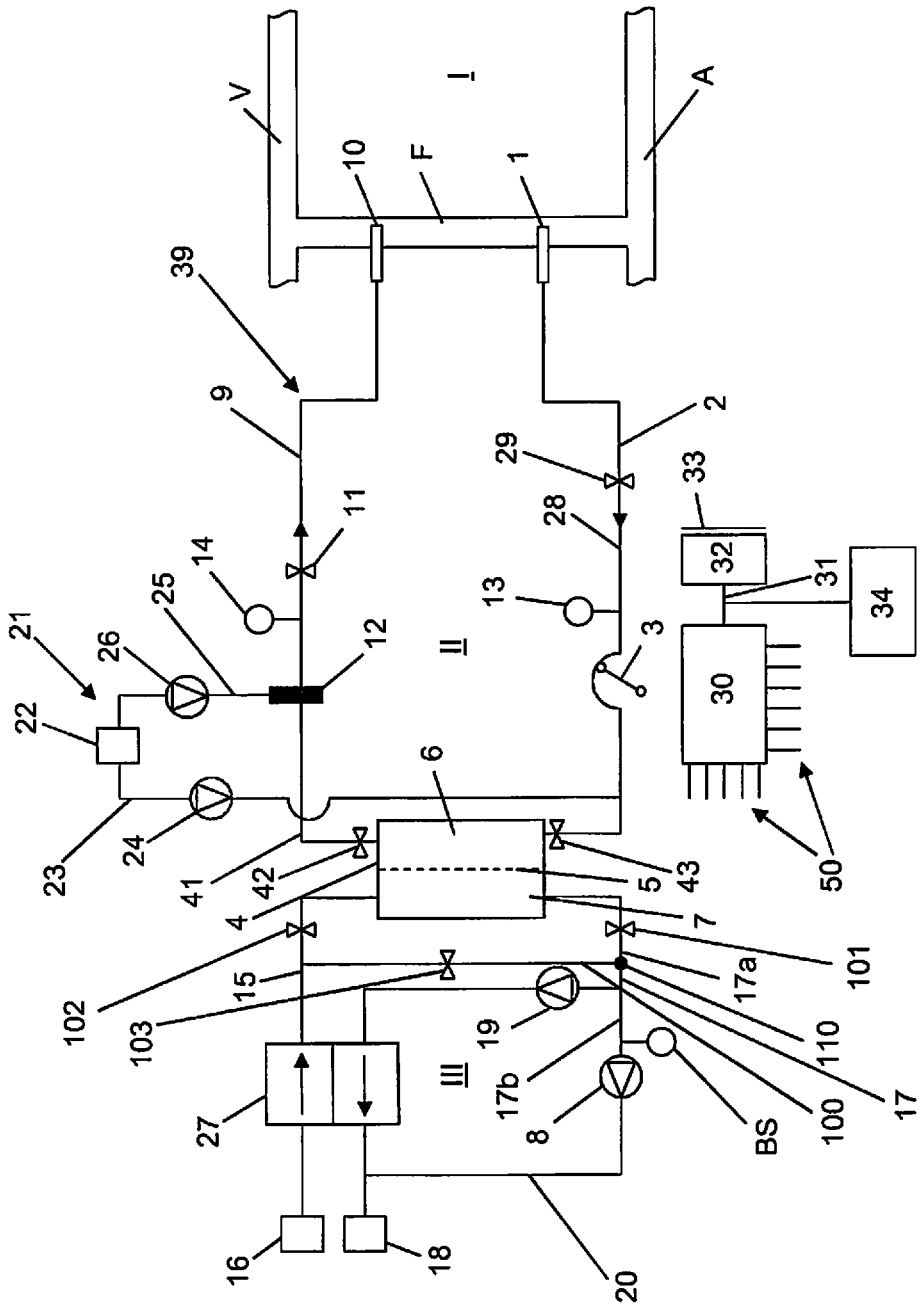

CONTROL UNIT FOR DETECTING BLOOD IN A DIALYSATE DISCHARGE LINE OF A BLOOD TREATMENT DEVICE, AND BLOOD TREATMENT DEVICE

The invention relates to a control unit for detecting blood in a dialysate discharge line of a blood treatment device, and also to a blood treatment device.

In methods for blood purification therapy, blood is conducted via an extracorporeal blood circuit. In the case of haemodialysis (HD), the blood is purified by a dialyser which has a blood chamber disposed in the extracorporeal blood circuit and also a dialysate chamber, which are separated from one another by a semipermeable membrane. Dialysate flows through the dialysate chamber during a haemodialysis treatment, wherein certain substances are transported through the membrane on account of the diffusion between the blood and the dialysate and are removed with the dialysate via a dialysate circuit. In the case of haemofiltration (HF), certain substances are filtered from the blood on account of convection through a filter membrane. Haemodiafiltration (HDF) is a combination of these two methods.

Fluid removed from the patient in the blood purification methods can be replaced by a substitution fluid, which is fed to the extracorporeal blood circuit during the treatment.

A dialysate pump is disposed in the dialysate circuit in order to convey the dialysate. An ultrafiltration pump generates the necessary negative pressure in the dialysate chamber of the dialyser so that fluid that is not replaced by substitution fluid can be removed from the patient in order to attain the desired fluid balance.

The membrane generally consists of hollow fibres. The integrity of the membrane ensures a separation of the blood from the dialysate.

In order to protect the patient, the known dialysis devices have different safety systems. A known safety system comprises a blood leak detector, which monitors the membrane of the dialyser for leaks which cause blood to pass from the blood circuit into the dialysate circuit. In the case of the known blood leak detectors, blood is detected in the dialysate generally by means of a photo-optical sensor, with which the concentration of blood in the dialysate, which is clear per se, can be determined. The blood leak detectors are operated multiple times in the flow and generate a signal when a predefined limit value is exceeded. In the event of a blood leak, in which case a predefined limit value is subsequently exceeded, various measures can be taken. An alarm can be triggered and the power supply of the blood pump can be interrupted. In some systems the dialysate side of the dialyser is also bypassed by means of a bypass line.

In this short-circuit situation, a dialysate supply line is directly connected to a dialysate discharge line, which during normal operation leads firstly into the dialysate chamber. This bypassing of the dialyser can be implemented by corresponding control for example of clamps, valves or other interruption means in the dialysate supply line, the dialysate discharge line, and the bypass line.

The blood leak detector is usually arranged downstream of a point of the dialysate discharge line at which the bypass line leads into the dialysate discharge line.

If the dialysate flows at higher speed through the dialysate discharge line, the absolute blood concentration in the dialysate discharge line is lower than with a slow flow rate. The blood volume passing over per unit of time is more strongly diluted. The limit value is therefore usually coupled to the flow rate in such a way that an undesirably high blood volume is detected by the blood volume passing through the membrane with the same absolute blood volume in the dialysate. The limit value thus decreases, for example inversely proportionally to the flow rate, because the sensitivity of the blood leak sensor must be increased with a stronger dilution of the blood.

If the dialysate no longer flows via the dialysate chamber on account of a corresponding control of clamping devices in the dialysate circuit, and instead flows via the open bypass line, the haemodialysis is stopped. With continued ultrafiltration taking place, fluid continues to be removed from the patient by the ultrafiltration pump and the negative pressure, generated thereby, in the dialysate chamber of the dialyser, which fluid also flows through the dialysate discharge line. If, in such a case, there is a blood leak in the dialyser, the relative blood concentration in the dialysate discharge line can rise significantly directly downstream of the dialyser, since no dialysate then flows into the dialyser. However, due to the opened bypass line, the dialysate continues to be pumped at the same speed as beforehand and dilutes the blood coming from the dialyser, which blood is enriched with dialysate, moreover heavily in the case of a blood leak. Thus, no blood leak is detected in the blood leak sensor when the diluted dialysate does not have a blood concentration above the limit value. In an extreme case, a heavy discolouration of the dialysate can be identified in the dialysate discharge line between dialyser and the point at which the dialysate discharge line leads into the bypass line, said discolouration being visible to the patient and the care staff. The fact that no alarm has yet been given may be interpreted incorrectly as a failure or malfunction of the blood leak detector, and may also lead to feelings of uncertainty, in particular for the patient.

The object of the present invention is to propose a method for detecting blood in a dialysate discharge line of a blood treatment device, which method detects an overshoot of a blood limit value downstream of the dialyser with and without bypass operation, and also to propose a control unit for carrying out said method.

The object is achieved by a control unit having the features described below. Advantageous embodiments are characterised below. A control unit according to the invention for detecting an overshoot of a first limit value of a first blood concentration in a first portion of a dialysate discharge line downstream of a dialysate chamber of a dialyser of a blood purification device and upstream of a node point at which a bypass line bypassing the dialyser leads into the dialysate discharge line, wherein the bypass line branches off, upstream of the dialysate chamber, from a dialysate supply line suitable for supplying dialysate from a dialysate source to the dialysate chamber, has a blood leak detector in a second portion of the dialysate discharge line downstream of the node point, which detector is suitable for detecting an overshoot of a second limit value of a second blood concentration in the second portion downstream of the node point and for communicating this to the control unit, wherein the second limit value decreases with increasing flow rate in the dialysate supply line before the branch point of the bypass line, and wherein the control unit is configured, in bypass operation, in which case the dialysate is guided from the dialysate source via the dialysate supply line, the bypass line, and the second portion of the dialysate discharge line, to consider the first limit value as having been overshot when the blood leak detector detects a third limit value as having been overshot, said third limit value being lower than the second limit value at the flow rate. Here, the flow rate denotes the flow rate associated with the corresponding second limit value.

The invention has the advantage that an undesirably high blood concentration in the first portion downstream of the dialyser can still be determined without providing an additional blood leak detector there.

In bypass operation, there is no longer any irritation to the patient or operator when there is no blood leak alarm triggered, in spite of detectable discolouration in the first portion.

Furthermore, a failure or a malfunction of the blood leak detector is not incorrectly determined, because said detector actually detects an excessively high blood concentration.

In accordance with one aspect of the invention, the control unit is configured such that the third limit value is independent of the flow rate of the dialysate in the dialysate supply line.

This enables an easily implemented limit value determination.

In accordance with a further aspect of the invention, the control unit is configured in such a way that the third limit value is a constant.

Only a single limit value advantageously has to be stored, which further reduces the complexity of the blood detection.

In accordance with one variant of the invention, the control unit is configured in such a way that with bypass operation a substitution rate of a pre-dilution is lower than a substitution rate limit value. The substitution rate relates to a pre-dilution as is known in the field of blood treatment devices. For this purpose, substitution fluid is fed in an extracorporeal blood circuit upstream to the blood chamber of the dialyser, as considered in the flow direction of the blood, an arterial blood supply line leading into said blood chamber. In the case of normal operation this causes the blood in the dialyser to be diluted before it is thickened again by an ultrafiltration in the dialyser. A reduction or complete stopping or pre-dilution further reduces the possible flow of dialysate in the first portion of the dialysate discharge line and can thus further intensify a visible clouding of the first portion of the dialysate discharge line.

In accordance with this variant it is advantageously ensured that an overshoot of the first limit value is reliably detected, also in the case of this even weaker dilution in the first portion of the dialysate discharge line.

For this purpose, in the case of reduced or stopped pre-dilution, the third limit value can advantageously be set even lower than with pre-dilution.

The described configuration applies accordingly in principle for the post-dilution, in which case merely the degree of the clouding may be different. The feed of the substitution fluid takes place in this case downstream of the blood chamber of the dialyser. The invention also includes this variant.

In accordance with a further aspect of the invention, the control unit is configured such that with bypass operation a dialysate flow through the dialyser is below a dialysate dialyser flow limit value. Bypass operation therefore does not have to mean a complete bypass of the dialyser, and instead a residual flow can remain through the dialysate supply line into the dialysate chamber of the dialyser.

The determination of a dialysate dialyser flow limit value has the advantage that, with a low residual flow through the dialyser, the use according to the invention of the low third limit value is utilised. Above the dialysate dialyser flow limit value, the control unit can usually use the second, flow-dependent limit value, in order to detect a blood leak in the event that said limit value is overshot.

A variant of the invention makes provision so that the control unit is configured in such a way that the flow rate is predefined by a pump device in the dialysate supply line.

This enables a simple determination of limit values.

In particular, the invention can make provision so that the control unit is configured in such a way that the flow rate is predefined by a balancing device.

A balancing device, such as a balanced chamber system, is known and does not need to be described here in greater detail. Put simply, the amount of dialysate supplied by the dialysate supply line and the amount of ultrafiltrate and also dialysate conducted away via the dialysate supply line can be selectively coordinated with one another. The flow rate in the dialysate supply line is determined via a filling and emptying of the balance chamber of the balancing device connected to this dialysate supply line.

If reference is made within the scope of the invention to the fact that the control unit or another suitable unit carries out something, this is a simplified way of expressing, and is to be understood to the extent that the control unit or the other suitable unit controls a suitable actuator or sensor as appropriate to carry out something if the control unit or the other suitable unit is not itself able to carry this out directly. A person skilled in the art will know in these cases that the corresponding simplified wording is to be understood accordingly.

By way of example, interruption means used conventionally in an extracorporeal blood circuit, such as hose clamps or valves, can be controlled as interruption means by the control unit.

The object set by the invention is also achieved with a blood treatment device described below.

A blood treatment device according to the invention for extracorporeal blood treatment, in particular for haemodiafiltration, is preferably intended to include a blood conduction system of an extracorporeal blood circuit, wherein the bloodstream system has an arterial portion of a blood supply line and a venous portion of a blood return line. The arterial portion and/or the venous portion are intended to be placed in fluid communication with a blood vessel, in particular an arteriovenous fistula, and the blood treatment device has at least one pressure generation device which is suitable for acting on the arterial and/or the venous portion.

A dialyser in the case of chronic blood purification therapy methods conducts blood via an extracorporeal blood circuit. In the case of haemodialysis (HD), the blood is purified by a dialyser which has a blood chamber disposed in the extracorporeal blood circuit and a dialysate chamber, which are separated from one another by a semipermeable membrane. Dialysate flows through the dialysate chamber during a haemodialysis treatment, wherein certain substances are transported through the membrane on account of the diffusion between the blood and the dialysate and are removed with the dialysate via a dialysate circuit. In the case of haemofiltration (HF), certain substances are filtered from the blood on account of convection through a filter membrane. Haemodiafiltration (HDF) is a combination of these two methods.

Fluid removed from the patient during the blood purification method can be replaced by a substitution fluid, which is supplied to the extracorporeal blood circuit during the blood treatment.

A dialysate pump is disposed in the dialysate circuit in order to convey the dialysate. An ultrafiltration pump generates the necessary negative pressure in the dialysate chamber of the dialyser so that fluid which is not replaced by substitution fluid can be removed from the patient in order to attain the desired fluid balance.

Here, the ultrafiltration pump during operation acts usually on the extracorporeal blood circuit in that a convection towards the dialysate chamber is created via a semipermeable membrane of a dialyser which separates a blood chamber from a dialysate chamber. This convection acts as negative pressure on the blood chamber of the dialyser and thus influences the extracorporeal blood circuit connected to the blood chamber. A pressure generation, which can act on the at least one portion, is also ended by a control and shutdown or stopping of the ultrafiltration pump. The way in which the corresponding pumps are provided in the dialysate circuit, in the blood conduction system and/or in the substitute conduction system with regard to the line into which they are introduced and their exact functionality during a blood treatment has no influence on the principle of the invention. Accordingly, the descriptions for conventional use of the ultrafiltration pump are not limiting, but are to be considered as merely exemplary. By way of example, the ultrafiltration pump can also be responsible only for the part of the ultrafiltration not compensated for by a substitution rate.

Furthermore, the blood treatment device according to the invention has a control unit according to the invention for detecting an overshoot of a first limit value of a first blood concentration in a first portion of a dialysate discharge line downstream of the dialysate chamber of the dialyser of the blood treatment device and upstream of the node point at which the bypass line bypassing the dialyser leads into the dialysate discharge line, wherein the bypass line branches off, upstream of the dialysate chamber, from a dialysate supply line suitable for supplying dialysate from a dialysate source to the dialysate chamber.

With the presence of a predetermined criterion, the control unit or the evaluation unit can deliver a notification. This notification can be provided for example via a signal generator. Accordingly, the control unit and/or evaluation unit can be configured to deliver the notification.

The invention and further advantageous variants and embodiments will be described in greater detail hereinafter on the basis of an exemplary embodiment with reference to the drawing.

The sole FIGURE, FIG. 1, schematically shows the structure of a haemodiafiltration device (HDF device) together with a control unit according to the invention for detecting an overshoot of a first limit value of a first blood concentration in a first portion of a dialysate discharge line downstream of a dialysate chamber of a dialyser.

On the basis of the drawing, the principle structure of a haemodiafiltration apparatus and connection thereof (merely indicated) to the vascular system I of a patient (not illustrated) will be briefly explained. In the case of haemodialysis, blood is conducted from the vascular system I into an extracorporeal blood circuit II. For this purpose, the patient is fitted with a fistula F, which forms a short circuit between an artery A and a vein V, for example in the left lower arm (not illustrated) and thus constitutes what is known as an arteriovenous fistula. A blood supply line 2 is connected to the fistula F via an arterial cannula 1. Blood from the vascular system I is supplied by means of a blood pump 3 via the blood supply line 2 to a blood purification element embodied as a haemodialyser 4. In the haemodialyser 4, a semipermeable membrane 5 preferably formed as a multiplicity of hollow fibres (not illustrated) separates a first chamber 6, which is also referred to as a blood chamber and which is part of the extracorporeal blood circuit II, from a second chamber 7, which is also referred to as a dialysate chamber and which is part of a dialysate circuit III. Substances to be removed from the blood pass over into the dialysate through the semipermeable membrane 5 and are carried away by the dialysate. At the same time, an excess fluid volume can be ultrafiltered from the blood via a pressure gradient and can also be removed via the dialysate flowing off. The pressure gradient is generated by an ultrafiltration pump 8.

The purified blood leaves the blood chamber 6 of the haemodialyser 4 via a blood return line 9 and is fed back via a venous cannula 10, which is inserted into a part of the fistula F facing towards the vein V of the patient, into the vascular system I of the patient. A venous clamp 11 is provided on the blood return line 9 as a venous interruption device, by means of which the return of blood can be interrupted, for example in emergency situations. Emergency situations of this type can occur for example when air is detected in the blood return line 9 by an air detector 12 between the dialyser 4 and venous clamp 11. An arterial pressure sensor 13 is provided on the blood supply line 2 upstream of the blood pump 3, and a venous pressure sensor 14 is provided on the blood return line 9 upstream of the venous clamp 11.

Dialysate flows through the second chamber 7 of the haemodialyser 4 and is supplied from a dialysate source 16 via a dialysate supply line 15 and is discharged to an outflow 18 via a dialysate discharge line 17. The dialysate is conveyed through a dialysate pump 19 in the dialysate discharge line 17. Upstream of the dialysate pump 19, an ultrafiltrate line 20 branches off from the dialysate discharge line 17, the ultrafiltration pump 8 being arranged in said ultrafiltrate line, which line also leads to the outflow 18.

In order to supply fluid back to the patient, the HDF apparatus has a substitution device 21, by means of which a substitution fluid (also referred to as substitute) can be supplied to the blood in the extracorporeal blood circuit II. The substitution device 21 has a substitute source 22 providing substitute, from which a first substitute line 23, in which a first substitute pump 24 is arranged, leads downstream of the blood pump 3 into the blood supply line 2, which is referred to as pre-dilution, since the substitute is supplied before the blood chamber 6. A second substitute line 25, in which a second substitute pump 26 is arranged, leads from the substitute source 22, downstream of the blood chamber 6 (post-dilation), into the blood return line 9. The second substitute line 25 leads into the drip chamber 12 of the return line 9.

Various balancing devices make it possible to selectively coordinate to one another the amount of substitute and dialysate which are supplied and the amount of ultrafiltrate and dialysate which are discharged, in cooperation with the aforementioned and possibly additional pumps. A wide range of embodiments are available to a person skilled in the art in order to provide a balancing device 27 which balances the supplied dialysate and discharged dialysate and also possibly further balancing devices and pumps in the dialysate circuit and in the substitute device, and therefore no detailed explanations are provided at this juncture. The same is also true for the provision of dialysate by the dialysate source 16 and for the provision of substitute by the substitute source 22.

There are also generally numerous possibilities available to a person skilled in the art for the use of actuators and sensors in an HDF apparatus, without the need to discuss all of these possibilities here in detail. The illustration in the drawing is limited to a few of these actuators and sensors sufficient for explanation of the invention, such as the clamp 103 in the bypass line 100, the blood leak detector BS, and the ultrafiltration pump 8.

The HDF apparatus is controlled and monitored by a control unit 30. The control unit 30 is for this purpose connected to the individual actuators and sensors of the apparatus by means of signal lines. This is indicated merely generally for the actuators and sensors illustrated in the drawing, such as pumps, pressure sensors, clamps, valves and blood leak detectors, by a multiplicity of signal lines 50, which are not illustrated individually for the individual actuators or sensors or detectors on account of the fact that this would result in an unclear depiction, and which are not denoted by individual reference signs.

The control unit according to the invention for determining the pressure in a blood vessel is explained in conjunction with the haemodiafiltration device that has just been described, since most or even all of the hardware components controlled in accordance with the invention, in particular actuators and sensors, are already provided therein. The invention, however, is not limited to the use of the control unit in the specifically described HDF device. The control unit can be part of the HDF apparatus or can form a separate unit which is to be connected to an existing HDF apparatus. However, the same is also true for any other blood treatment device, for example a haemofiltration apparatus and a haemodialysis apparatus, to which a control unit according to the invention can be connected The method steps explained hereinafter as being carried out by the control unit can also either all be controlled by the control unit according to the invention or can be selectively carried out manually at least in part within the scope of the method according to the invention, or can be carried out by further devices, such as an evaluation unit, a storage unit, an input unit, a signal generator, or further devices which in turn carry out steps after control by the control unit or in a manually operated manner or independently.

If reference is made hereinafter to the fact that the control unit or another suitable unit "carries out" something, for example measures a blood concentration or closes a clamp, this is a simplified way of expressing, and is to be understood to the extent that the control unit or the other suitable unit controls a suitable actuator or sensor as appropriate to carry out something, possibly after querying a status, for example to control a blood detector, measure a blood concentration and communicate the measured blood concentration to the control unit, or control a clamp so as to close said clamp, possibly after querying whether this is already closed, etc. For the sake of completeness, it is not in all cases specified which actuator or sensor is active after control. In these cases a person skilled in the art will understand the corresponding simplified wording.

The further configurations of the control unit will be presented hereinafter within the scope of the method according to the invention.

In accordance with the exemplary embodiment of the method according to the invention, the patient is firstly in a running haemodiafiltration method. This means that the blood pump 3 pumps blood from the fistula F through the blood supply line 2 into the first chamber 6 of the haemodialyser 4 and via the blood return line 9 and the venous cannula 10 back into the fistula F. The venous clamp 11 and the arterial clamp 29 in the blood supply line are opened as arterial interruption device. Undesirable constituents are removed from the blood by the haemodialyser 4 and the blood is thus purified.

A flow Q1 is set in the dialysate supply line by the balancing device 27. The blood leak detector measures the second blood concentration B2 in the second portion 17b of the dialysate discharge line 17 downstream of the node point 110 at which the bypass line 100 leads into the dialysate discharge line 17, and communicates the value of the second blood concentration B2 to the control unit 30. Depending on the flow rate Q1, the control unit provides a second limit value G2. If, by way of example as a result of a membrane rupture, blood passes through the membrane 5 into the dialysate chamber 7, this is pumped in the corresponding concentration via the dialysate discharge line 17 to the blood leak detector BS. If a second blood concentration B2 is measured there that is higher than the limit value G2, this is detected by the control unit 30. The control unit 30 by way of example now generates an alarm signal and/or stops the blood pump 3 or otherwise provides a response. These can be routine measures, for example an optical display.

Within the scope of the exemplary embodiment, a switchover is made to bypass operation during dialysis operation. For this purpose, the clamps 101 and 102 are closed and the bypass line 100 is opened by opening the valves 103. The dialysate is then pumped at a balancing chamber 27, which continues to operate, at the same flow as before via the bypass line 100. However, the dialysate no longer flows through the dialysate chamber 7, and therefore no dialysis by diffusion takes place. On account of the ultrafiltration pump 8 however, which continues to run, a haemofiltration continues to be operated. Plasma fluid passes over from the blood chamber 6 into the dialysate chamber 7 via the membrane 5 and flows via the dialysate discharge line 17 in the direction of the outflow 18. Even in the case of an average rupture, a severe discolouration can occur in the first portion 17a of the dialysate discharge line 17a, since only a weak dilution of the blood takes place on account of the low flow effected merely by the UF pump 8. When a switchover is made into bypass operation, the control unit has taken on a stored third limit value G3 as limit value for a blood leak alarm, which limit value is in this example a constant much lower than the second limit value G2 provided with the present flow Q1, for example is half the value of the second limit value G2. Due to this significantly increased sensitivity, the control unit thus triggers an alarm when the blood concentration indeed still lies far below the second limit value G2 due to the dilution of the dialysate subsequently supplied via the bypass line 100, but there is a discoloration of the dialysate in the first portion 17a of the dialysate discharge line 17 clearly visible to the patient and operator.

In one variant of the exemplary embodiment, the control unit 30 is configured to control and stop the pre-dilution pump 24 in bypass operation. There is thus also no dilution of the dialysate in the dialysate discharge line 17 by substitute. In this case, a further limit value G3' can be provided or stored, which is lower still, for example two thirds of G3. The lower the dilution of the dialysate in the dialysate discharge line 17, the lower can be the limit value G3.

The invention is not limited to the described exemplary embodiments. In particular, any type of blood leak detector which detects blood or blood constituents, in particular such as haematocrit, can be used in accordance with the invention. In addition, all specified features can be combined arbitrarily with one another, provided this is sensible and feasible within the scope of the invention. Individual steps or sub-steps of the method can all be carried out by the control unit.

The control unit does not always have to be the same, individual control unit. Rather, a first control unit can carry out the steps necessary for the blood leak detection, such as limit value querying, detection of the limit value overshoot, triggering of an alarm, etc. A second control unit can control the remaining processes necessary for the blood treatment. This can be the control of actuators and sensors, etc. Other sub-units, such as storage units, display units, computing units, etc., are also included by the term 'control unit'.

The invention claimed is:

1. A blood treatment device for extracorporeal blood treatment comprising
   a dialyser having a dialysate chamber,
   a dialysate discharge line,
   a control unit for detecting an overshoot of a first limit value of a first blood concentration in a first portion of the dialysate discharge line downstream of the dialysate chamber and upstream of
   a node point at which
   a bypass line bypassing the dialyser leads into the dialysate discharge line, wherein the bypass line branches off at a branch point, upstream of the dialysate chamber, from
   a dialysate supply line for supplying dialysate from a dialysate source to the dialysate chamber,
   a blood leak detector provided in a second portion of the dialysate discharge line downstream of the node point for measuring a second blood concentration in the second portion downstream of the node point, and in the absence of a blood leak detector in the first portion of the dialysate discharge line,
wherein the control unit detects an overshoot of a second limit value of the second blood concentration, wherein the second limit value decreases with rising flow rate in the dialysate supply line before the branch point of the bypass line, and wherein the control unit is configured, in the event of bypass operation, in which case dialysate is guided from the dialysate source via the dialysate supply line, the bypass line, and the second portion of the dialysate discharge line to an outflow, to consider the first limit value as having been overshot when the second blood concentration exceeds a third limit value, which is lower than the second limit value at the flow rate, and wherein the control unit is configured to trigger an alarm and/or to stop a blood pump when the second blood concentration exceeds the third limit value.

2. The blood treatment device according to claim 1, characterised in that the control unit is configured in such a way that the third limit value is independent of the flow rate.

3. The blood treatment device according to claim 1, characterised in that the control unit is configured in such a way that the third limit value is a constant.

4. The blood treatment device according to claim 1, characterised in that the control unit is configured in such a way that in bypass operation a substitution rate of a pre-dilution is lower than a substitution limit value.

5. The blood treatment device according to claim 1, characterised in that the control unit is configured in such a way that in bypass operation a dialysate flow through the dialyser is below a dialysate dialyser flow limit value.

6. The blood treatment device according to claim 1, characterised in that the control unit is configured in such a way that the flow rate is predefined by a pump device in the dialysate supply line.

7. The blood treatment device according to claim 1, characterised in that the control unit is configured in such a way that the flow rate is predefined by a balancing device.

* * * * *